United States Patent [19]
Berg

[11] Patent Number: 5,885,259
[45] Date of Patent: Mar. 23, 1999

[54] INCREASING RADIUS CURVE CATHETER

[75] Inventor: Todd A. Berg, Lino Lakes, Minn.

[73] Assignee: SciMed Life Systems, Inc., Maple Grove, Minn.

[21] Appl. No.: 895,662

[22] Filed: Jul. 17, 1997

Related U.S. Application Data

[63] Continuation of Ser. No. 588,779, Jan. 19, 1996, abandoned.

[51] Int. Cl.⁶ ................................................ A61M 25/00
[52] U.S. Cl. .................................... 604/281; 604/280
[58] Field of Search ...................... 604/264, 280, 604/281, 95; 600/433–435

[56] References Cited

U.S. PATENT DOCUMENTS

| | | | |
|---|---|---|---|
| 3,935,857 | 2/1976 | Co | 128/2.05 |
| 3,938,501 | 2/1976 | Erikson | 128/2 A |
| 4,020,829 | 5/1977 | Willson et al. | 128/2 M |
| 4,033,331 | 7/1977 | Guss et al. | 128/2 M |
| 4,117,836 | 10/1978 | Erikson | 128/2.05 R |
| 4,169,464 | 10/1979 | Obrez | 128/657 |
| 4,195,637 | 4/1980 | Gruntzig et al. | 128/348 |
| 4,292,976 | 10/1981 | Banka | 128/656 |
| 4,430,083 | 2/1984 | Ganz et al. | 604/283 |
| 4,547,193 | 10/1985 | Rydell | 604/262 |
| 4,551,292 | 11/1985 | Fletcher et al. | 264/139 |
| 4,563,181 | 1/1986 | Wijayarathna et al. | 604/280 |
| 4,568,338 | 2/1986 | Todd | 604/281 |
| 4,733,669 | 3/1988 | Segal | 128/663 |
| 4,738,667 | 4/1988 | Galloway | 604/281 |
| 4,747,840 | 5/1988 | Lakika et al. | 604/280 |
| 4,781,682 | 11/1988 | Patel | 604/96 |
| 4,784,639 | 11/1988 | Patel | 604/53 |
| 4,790,831 | 12/1988 | Skribiski | 604/282 |
| 4,813,930 | 3/1989 | Elliott | 604/53 |
| 4,820,349 | 4/1989 | Saab | 128/344 |
| 4,822,345 | 4/1989 | Danforth | 604/282 |
| 4,867,174 | 9/1989 | Skribiski | 128/772 |
| 4,882,777 | 11/1989 | Narula | 604/281 |
| 4,883,058 | 11/1989 | Ruiz | 128/654 |
| 4,886,506 | 12/1989 | Lovgren et al. | 604/280 |
| 4,898,577 | 2/1990 | Badger et al. | 604/53 |
| 4,898,591 | 2/1990 | Jang et al. | 604/282 |

(List continued on next page.)

FOREIGN PATENT DOCUMENTS

| | | |
|---|---|---|
| 0 132 344 A2 | 1/1985 | European Pat. Off. . |
| 256 478 A1 | 2/1988 | European Pat. Off. . |
| 0 277 366 A1 | 8/1988 | European Pat. Off. . |
| 0 323 738 A2 | 7/1989 | European Pat. Off. . |
| 0 656 217 A1 | 6/1995 | European Pat. Off. . |
| 0 727 236 A1 | 8/1996 | European Pat. Off. . |
| WO 92/12754 | 8/1992 | WIPO . |
| WO 93/14802 | 8/1993 | WIPO . |
| WO 95/08364 | 3/1995 | WIPO . |

OTHER PUBLICATIONS

USCI Block™ Right Coronary Guiding Catheter, 1989, 2 pages.

USCI Video Tape ("Select Curve Guiding Catheter: Cannulating the Right Coronary Artery") transcrpit and selected figures, 1988.

USCI Video Tape: *Select Curve Guiding Catheter: Cannulating the Right Coronary ARtery,* USCI, C.R. Bard, 1988.

*USCI Gruntzig Dilaca Coronary Dilatation Equipment,* USCI, C.R. Bard, Inc. 1990, 4 pages.

(List continued on next page.)

*Primary Examiner*—Mark Bockelman
*Attorney, Agent, or Firm*—Crompton, Seager & Tufte, LLC

[57] ABSTRACT

A guide catheter for insertion into the cardiovascular system having a straight portion and an improved distal end portion for more precise and easier positioning in a left coronary artery. The improved distal portion includes a secondary curved portion, followed distally by a primary curved portion, terminating with a distal tip portion. The primary and secondary curved portions are constructed such that the primary and secondary curved portions have an approximately equal curvature radii when the distal tip portion is positioned in the ostium of the left coronary artery, thereby forming a constant radius curve.

14 Claims, 2 Drawing Sheets

U.S. PATENT DOCUMENTS

| | | | |
|---|---|---|---|
| 4,909,787 | 3/1990 | Danforth | 604/95 |
| 4,925,445 | 5/1990 | Sakamoto et al. | 604/95 |
| 4,935,004 | 6/1990 | Cruz | 604/29 |
| 4,935,017 | 6/1990 | Sylvanowicz | 604/280 |
| 4,950,228 | 8/1990 | Knapp, Jr. et al. | 604/8 |
| 4,976,691 | 12/1990 | Sahota | 128/772 |
| 4,981,477 | 1/1991 | Schon et al. | 604/264 |
| 4,983,166 | 1/1991 | Yamawaki | 604/96 |
| 4,994,032 | 2/1991 | Sugiyama et al. | 604/96 |
| 5,000,743 | 3/1991 | Patel | 606/194 |
| 5,035,686 | 7/1991 | Crittenden et al. | 604/96 |
| 5,044,369 | 9/1991 | Sahota | 128/658 |
| 5,045,072 | 9/1991 | Castillo et al. | 604/280 |
| 5,058,595 | 10/1991 | Kern | 128/662 |
| 5,059,197 | 10/1991 | Urie et al. | 606/116 |
| 5,098,412 | 3/1992 | Shiu | 604/280 |
| 5,122,125 | 6/1992 | Deuss | 604/282 |
| 5,163,921 | 11/1992 | Feiring | 604/247 |
| 5,188,619 | 2/1993 | Myers | 604/280 |
| 5,195,990 | 3/1993 | Weldon | 604/281 |
| 5,203,776 | 4/1993 | Durfee | 604/264 |
| 5,215,540 | 6/1993 | Anderhub | 604/281 |
| 5,267,982 | 12/1993 | Sylanowicz | 604/281 |
| 5,299,574 | 4/1994 | Bower | 128/658 |
| 5,306,262 | 4/1994 | Weldon | 604/281 |
| 5,306,263 | 4/1994 | Voda | 604/281 |
| 5,401,258 | 3/1995 | Voda | 604/281 |
| 5,445,625 | 8/1995 | Voda | 604/281 |
| 5,603,704 | 2/1997 | Bin et al. | |

OTHER PUBLICATIONS

USCI "Positrol II and Nycore™ Cardiovascular Catheter" pp. 1–21.

King SB, III and Douglas S. Jr.: *Coronary Arteriography and Angioplasty*, McGraw–Hill, New York, Chapter 17, *Percutaneous Transluminal Coronary Angioplasty*, pp. 433–460, 1985.

Amplatz, K., et al. *Mechanics of Selective Coronary Artery Catheterization via Femoral Approach*, Radiology 89: 1040–1047, Jul. 1967.

Judkins, M., *Percutaneous Transfemoral Selective Coronary Arteriography*, Radiologic Clinics of North America—vol. VI, No. 3, Dec. 1968, pp. 467–492.

Carr, M., *The Use of the Guiding Catheter in Coronary Angioplasty: The Technique of Manipulating Catheters to Obtain the Necessary Power to Cross Tight Coronary Stenoses*, Catheterization and Cardiovascular Diagnosis 12: 189–197, 1986.

"Coronary Arteriography and Angioplasty", Spencer B. King, III and John S. Douglas pp. 182–238.

Medi–tech—Boston Scientific Corporation "Imager Angiographic Catheters" brochure, Oct. 1990.

Mallinckrodt "Diagnostic Catheters" brochure, Oct. 1990, 1 page.

Bourassa "Cardiovascular Catheters Sterile" brochure, Jun. 1972, 4 pages.

USCI "KIFA Products" brochure, pp. 1–12, Jun., 1974.

USCI KIFA Products "Catheterization Equipment" brochure pp. 1–7, 1967.

Arani STE: *A New Catheter for Angioplasty of the Right Coronary Artery and Aortocoronary Bypass Grafts*, Cath. Cardiovasc. Diagn. 11:647–653, 1985.

Block, PC et al.: *PTCA in Perspective*, USCI Division, C.R. Bard, Inc. Billerica MA, pp. 23–42, 1986.

"Angled Tip of the Steerable Guidewire and Its Usefulness in Percutaneous Transluminal Coronary Angioplasty", Jan Voda, *Use of Angled Guidewires in PTCA*, 1987, pp. 204–210.

Wilson et al., Biplane Selective Coronary Arteriography Via Percutaneous Transfemoral Approach, presented at the Sixty–Seventh Annual Meeting of the American Roentgen Ray Society, San Francisco, California, Sep. 27–30, 1966.

El Gamal et al., Improved Success Rate of Percutaneous Transluminal Graft and Coronary Angioplasty with the El Gamal Guiding Catheter, *Catheterization and Cardiovascular Diagnosis*, 11;89–96 (1985).

SciMed Life Systems, Inc. *Guide Catheter Training*, 1990.

INCREASING RADIUS CURVE CATHETER

This application is a continuation of application Ser. No. 08/588,779, filed Jan. 19, 1996, now abandoned.

BACKGROUND OF THE INVENTION

This invention relates generally to catheters adapted to be inserted into the cardiovascular system and, more particularly, to an improved guide catheter having a distal end portion for more precise and easier positioning in the left coronary artery.

Catheters are often advanced in the performance of medical procedures such as angioplasty to widen the lumen of a coronary artery which has become at least partially blocked by a stenotic lesion causing an abnormal narrowing of the artery due to injury or disease. In these techniques, an angioplasty catheter is usually introduced into the aorta and then the coronary artery through a previously placed guide catheter. To place the guide catheter in the coronary artery, the proximal end of the guide catheter is manipulated until its distal end is steered into the ostium of the coronary artery branching off from the aorta. Other therapeutic catheters such as atherectomy catheters may also be advanced through the guide catheter.

A commonly used guide catheter used in treatment of the left coronary artery is often referred to as a "Judkins" catheter which has a specially shaped distal end portion for facilitating insertion into the left coronary artery. The Judkins catheter, from proximal to distal end, comprises a long first straight portion, a 180 degree curved portion, a shorter second straight portion parallel to the first straight portion, a bend a distal tip portion perpendicular to the second straight portion. The Judkins catheter forms relatively large angles when inserted into the cardiovascular system.

An improvement on the Judkins catheter includes a straight portion followed distally by a curved portion, followed distally by a second straight portion, followed distally by a second curved portion, followed distally by a tip. This straight portion lies against the ascending aorta wall opposite the ostium of the left coronary artery, providing support for the catheter. This improved design allows for better coaxial alignment in the lumen of the selected artery.

An angioplasty or other therapeutic catheter advanced through a guide catheter having numerous transitions between the straight and curved portions, or curves of varying radii encounter some resistance to advancement at each of the transitions. More specifically, when a therapeutic catheter encounters a transition point or bend in a guide catheter, this results in a force by the guide catheter tending to make the intravascular catheter assume the path of the guide catheter. There is an opposite force by the intravascular catheter tending to make the guide catheter assume the path of the intravascular catheter. In the region of the ascending aorta, a therapeutic catheter advanced through the transitions in the guide catheter will tend to straighten out the guide catheter curve and dislodge the guide catheter tip portion from the ostium of the left coronary artery. If the tip is dislodged from the ostium, time consuming replacement of the tip of the guide catheter into the ostium may be required.

SUMMARY OF THE INVENTION

The present invention pertains to a guide catheter having a substantially constant radius curve when the distal tip of the catheter is positioned in the ostium of the left coronary artery. The constant radius curve has no significant bends or transition points while in this position. This improved shape reduces the resistance by the guide catheter against the advance of the therapeutic catheter, where the opposing force by the advancing therapeutic catheter acts to straighten out the guide catheter and pull it from its desired position. This easier advance of the intravascular catheter means there is less force tending to dislodge the distal tip of the guide catheter from the ostium of the left coronary artery.

In a preferred embodiment, the guide catheter in accordance with the present invention is for a catheter having a proximal end, a straight portion extending distally, and a curved portion. The curved portion has a secondary curved region, a primary curved region, and a distal end, where the primary and secondary curves have unequal radii ex vivo but form a single continuous curve when the distal end is inserted in the ostium. Consequently, less force is required to advance a therapeutic catheter through the guide catheter than through a guide catheter with transitions in curve radii.

The guide catheter can be made from materials such as polymers, which exhibit sufficient softness and flexibility to be steerable to the coronary artery, yet rigid enough to permit the transmission of twisting forces along its length by manipulation of its proximal end. Such materials and methods of fabrication are well known in the art.

BRIEF DESCRIPTION OF THE DRAWINGS

The above brief description, as well as further objects, features and advantages of the present invention will be more fully appreciated by reference to the following detailed description of the presently preferred, but nonetheless embodiments, in accordance with the present invention when taken into conjunction with the accompanying drawings wherein.

DESCRIPTION OF THE PRIOR ART

Figure 1:
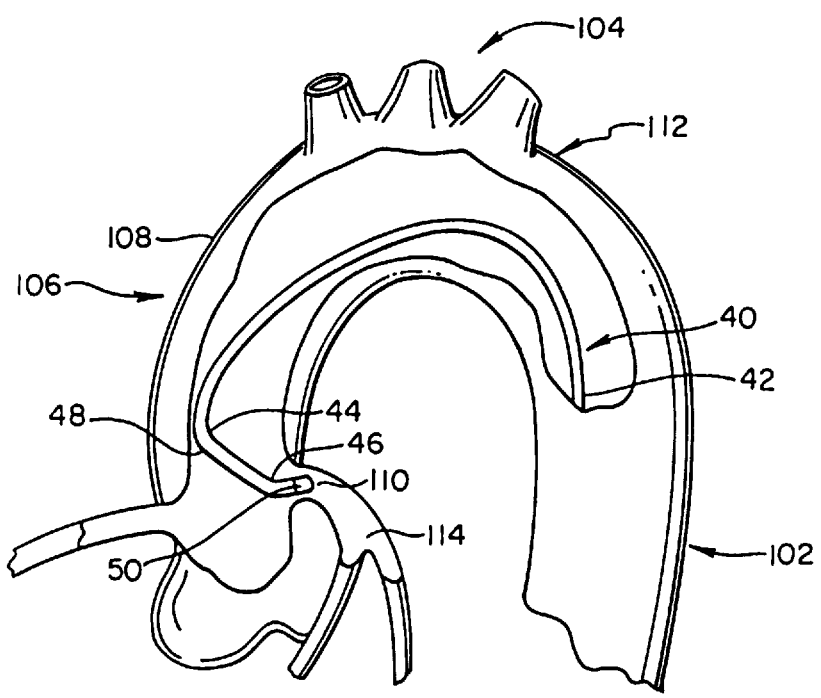
FIG. 1 is a cross sectional view of a cardiovascular system with a prior art catheter positioned with the catheter distal tip positioned in the ostium of the left coronary artery.

Referring to FIG. 1 of the drawings, the reference numeral 40 refers, in general, to a prior art guide catheter. Catheter 40 is in the form of an elongated tubular member having a straight portion 42, and a distal end portion consisting of a secondary curved portion 44, a transition 48, a primary curved portion 46, and a distal tip 50.

Secondary curved portion 42 and primary curved portion 46 have in vivo radii of curvature such that the secondary radius of curvature is larger than the primary radius of curvature resulting in a pronounced transition 48 which presents increased resistance to devices advancing through the guide catheter curved shape.

DESCRIPTION OF THE PREFERRED EMBODIMENT

Figure 2:
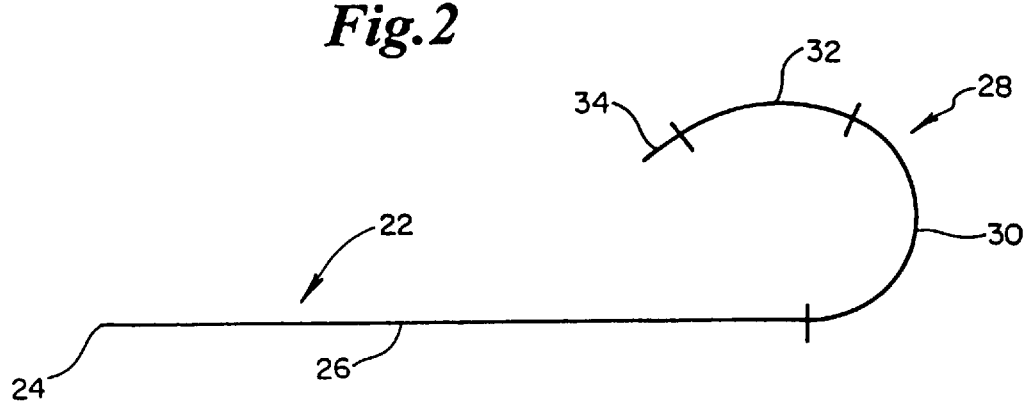
FIG. 2 is a side view of an embodiment of the instant invention catheter, ex vivo.
Figure 3:
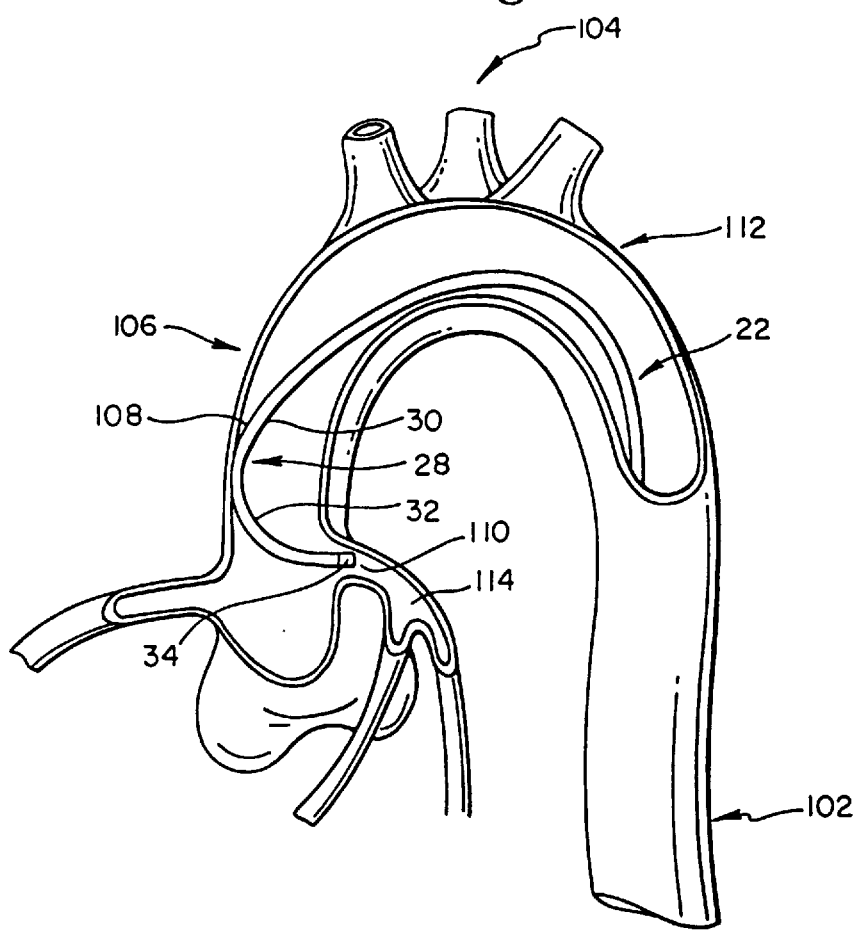
FIG. 3 is a cross sectional view of a cardiovascular system with an embodiment of the instant invention catheter positioned with the catheter distal tip positioned in the ostium of the left coronary artery.

A guide catheter in accordance with the present invention is shown in general by reference numeral 22 in FIGS. 2 and 3. Guide catheter 22 of the present invention is configured to overcome the aforementioned deficiency of resistance to advancement of intravascular catheters and the resultant tendency to dislodge a guide catheter distal tip.

FIG. 2 shows the ex vivo structure of the catheter. Guide catheter 22 has a proximal end 24 and a distal tip 34. Extending from proximal end 24 is a straight portion 26, where straight portion 26 is sufficiently long to reach from the arterial point of insertion to the aortic arch 112. In one embodiment of e present invention, where guide catheter 22 is inserted into the femoral artery near the groin, the length of straight portion 26 is approximately 36 inches. Extending distally from straight portion 26 is, in turn, a curved portion 28, which begins with a secondary curve portion 30 followed by a primary curve portion 32. Secondary curve portion 30 has a radius of curvature, Sr, and primary curve portion 32 has a radius of curvature, Pr.

In one embodiment of the invention, secondary curve portion 30 has a radius of curvature of 0.6 inches, describing an angle of 155 degrees, and primary curve portion 32 has a radius of curvature of 0.9 inches, describing an angle of 60 degrees. Some embodiments of the invention have Pr and Sr such that the ex vivo Pr/Sr ratio are in the range of 1.3 to 2.0. It can be appreciated that these elements of the present invention may have different dimensions.

Distal tip portion 34 follows primary curve portion 32. In one embodiment of the invention, distal tip portion 34 extends tangentially from primary curve portion 32. In another embodiment of this invention, there is a bend (not shown) between primary curve portion 32 and distal tip portion 34.

FIG. 3 illustrates the placement of the present invention in vivo. Catheter 22 is normally inserted through aorta 102 by inserting catheter 22 in the femoral artery near the groin. Catheter 22 lies in the aortic arch 112, with distal tip portion 34 coaxially within the ostium 110 of the left coronary artery 114. Straight portion 26 which was straight ex vivo, is curved somewhat in vivo and extends over the aortic arch 112. Secondary curve portion 30 radius of curvature in vivo is larger than the radius of curvature ex vivo. This increased in vivo secondary curve portion 30 radius now closely matches the radius of the primary curve portion 32. The substantially equal radius of primary curve portion 32 and secondary curve portion 30 form essentially a single curve with a substantially constant radius.

The aforementioned constant radius curve lies in the aorta 102, preferably lying against the inner wall of the ascending aorta 106 opposite the ostium 110 of the left coronary artery 114. As a result of this constant radius curve, an intravascular catheter advancing through catheter curved portion 28 encounters insubstantial transition points, rather than encountering resistance at such points which would tend to dislodge a distal tip portion from the ostium of the left coronary artery.

It is understood that several variations may be made in the foregoing without departing from the scope of the invention. For example, the specific lengths and angles of the present invention can be varied within the scope of the invention. Moreover, it is understood that, instead of the identical radii of curvature and angles shown and described in the above examples, the catheters of the present invention can vary. For example, for patients with different sizes and geometries, the radii and angles may vary to achieve the in vivo constant curve guide catheter of FIG. 3.

What is claimed is:

1. A catheter for insertion through the aorta to reach the ostium of the left coronary artery, the aorta having an inner wall opposite the ostium, said catheter comprising:
   an elongated tubular member including;
      a proximal end,
      a straight portion extending distally from said proximal end, and
      a curved portion extending distally from said straight portion;
   said curved portion including;
      a secondary curve portion, said secondary curve portion having a radius of curvature, Sr, and
      a primary curve portion disposed distally of said secondary curved portion, said primary curve portion having a radius of curvature, Pr; and
   wherein, when the distal end of said catheter is positioned in the ostium of the left coronary artery, said curved portion engages the opposite inner aortic wall and said Pr is approximately equal to said Sr, and when said catheter is in the ex vivo state, said Pr is greater than said Sr.

2. The catheter of claim 1, wherein when said catheter is in the ex vivo state, said Pr is greater than or equal to said Sr.

3. The catheter of claim 2, wherein said primary curve and secondary curve have the ratio Pr/Sr; and the ex vivo Pr/Sr ratio is in the range 1.3 to 1.8.

4. The catheter of claim 2, wherein said primary curve and secondary curve have the ratio Pr/Sr; and the in vivo ratio is close to 1.0.

5. A catheter for insertion through the aorta to reach the ostium of the left coronary artery, said catheter comprising:
   an elongate tubular member having a proximal end and a distal end;
   said tubular member including a straight portion extending distally from said proximal end; and
   said catheter including curve means, extending distally from said straight portion and being disposed proximally of the distal end, for positioning said distal end of said catheter into the left coronary ostium such that the curved means has a substantially non-constant radius of curvature when said catheter is in the ex vivo state and a substantially constant radius of curvature when said catheter distal end is positioned in said left coronary artery ostium and at least a portion of said curve means is positioned against said aorta wall.

6. The catheter of claim 5, wherein said curve means further comprises:
   a secondary curve portion extending distally from said straight portion, said secondary curve portion having a radius of curvature, Sr, and
   a primary curve portion extending distally from said secondary curve portion, said primary curve portion having a radius of curvature, Pr,
   wherein, when said catheter distal end is positioned in said left coronary artery ostium, said Pr is approximately equal to said Sr,
   wherein, when said catheter is in the ex vivo state, said Pr different from said Sr.

7. The catheter of claim 6, wherein when said catheter is in the ex vivo state, said Pr is greater than said Sr.

8. The catheter of claim 6, wherein when said catheter is in the ex vivo state, said Pr is greater than or equal to said Sr.

9. The catheter of claim 8, wherein said primary curve and said secondary curve have the ratio Pr/Sr, and the ex vivo Pr/Sr ratio is in the range 1.3 to 1.8.

10. The catheter of claim 8, wherein said primary curve and said secondary curve have the ratio Pr/Sr, and the in vivo Pr/Sr ratio is close to 1.0.

11. A catheter for insertion through the aorta to reach the ostium of the left coronary artery, said catheter comprising:

an elongated tubular member including,
  a proximal end,
  a straight portion extending distally from said proximal end, and
  a curved portion extending distally from said straight portion;
said curved portion including;
  a secondary curve portion extending distally from said straight portion, said secondary curve portion having a radius of curvature, Sr, and
  a primary curve portion extending distally from said secondary curve portion, said primary curve portion having a radius of curvature, Pr,
  wherein said Pr and said Sr have an ex vivo ratio Pr/Sr in the range of 1.3 to 2.0.

12. The catheter of claim 11, wherein said Pr is 0.9 inches and said Sr is 0.6 inches.

13. The catheter of claim 12, wherein said primary curve portion describes an angle of 60 degrees and said secondary portion describes an angle of 155 degrees.

14. The catheter of claim 11, wherein said primary curve portion describes an angle of 60 degrees and said secondary curve portion describes an angle of 155 degrees.

* * * * *

UNITED STATES PATENT AND TRADEMARK OFFICE
CERTIFICATE OF CORRECTION

PATENT NO. : 5,885,259
DATED : March 23, 1999
INVENTOR(S) : Todd A. Berg

It is certified that error appears in the above-identified patent and that said Letters Patent is hereby corrected as shown below:

Column 4, line 18, delete "or equal to".

Signed and Sealed this

Twentieth Day of June, 2000

Attest:

Q. TODD DICKINSON

*Attesting Officer*                    *Director of Patents and Trademarks*